United States Patent
Lloyd

[11] Patent Number: 5,938,602
[45] Date of Patent: Aug. 17, 1999

[54] CATHETER TRACKING SYSTEM AND METHOD

[75] Inventor: Peter Gregory Lloyd, Southampton, United Kingdom

[73] Assignee: Roke Manor Research Limited, Romsey, United Kingdom

[21] Appl. No.: 08/867,878

[22] Filed: Jun. 3, 1997

[30] Foreign Application Priority Data

Jun. 11, 1996 [GB] United Kingdom .................... 9612199
Aug. 1, 1996 [GB] United Kingdom .................... 9616234

[51] Int. Cl.⁶ ....................................................... A61B 5/00
[52] U.S. Cl. ............................................. 600/424; 607/122
[58] Field of Search ..................................... 600/424, 407, 600/437; 607/122; 128/899

[56] References Cited

U.S. PATENT DOCUMENTS 4,706,681  11/1987  Breyer et al. .
4,821,731   4/1989  Martinelli et al. .
4,896,673   1/1990  Rose et al. .
5,135,001   8/1992  Sinofsky et al. .

FOREIGN PATENT DOCUMENTS 0419729       4/1991  European Pat. Off. .
2189030      10/1987  United Kingdom .
90/11722     10/1990  WIPO .
92/03972      3/1992  WIPO .
95/07657      3/1995  WIPO .
WO 95/28884  11/1995  WIPO .

*Primary Examiner*—Ruth S. Smith
*Attorney, Agent, or Firm*—Evenson, McKeown, Edwards & Lenahan, PLLC

[57] ABSTRACT

A catheter tracking system for tracking and monitoring a position of a catheter head within the human or animal body includes a self-referencing catheter. The self-referencing catheter includes an inner core, an outer sheath having a plurality of sensors and a cage for fixing the outer sheath at a predetermined position. The sensors receive signals generated by the transducer so as to produce measurement signals in accordance with a time of propagation of the signals for determining the position of the head relative to the outer sheath.

26 Claims, 3 Drawing Sheets

CATHETER TRACKING SYSTEM AND METHOD

BACKGROUND OF THE INVENTION

The present invention relates to catheter tracking systems, which operate to determine a position of a catheter within the human or animal body.

Furthermore, the invention relates to a method for tracking a catheter within the human or animal body.

Electro-cardiography is a process for recording electrical signals created by a heart, using electrodes applied externally and, more particularly, electrodes positioned on tips of catheters inserted within the heart. In known endocardial catheter technology great use is made of in-theatre fluoroscopy to locate and guide the catheters to positions within the heart where measurements are required. The use of fluoroscopy has a disadvantage that inevitably theatre staff and the patient are exposed to X-ray radiation.

In order to circumvent this disadvantage, an endocardial catheter tracking system has been recently proposed, in which an AC magnetic field generated by a set of three coils mounted below the patient within the structure of a theatre table is used to track a tip of a catheter provided with a magnetic sensor. The system is complicated by the fact that the patient may move on the table and thus destroy the accuracy in the measurement of the position of the catheter tip relative to the heart. In order to overcome this problem a further catheter is used which also carries a magnetic sensor. This catheter is referred to as a reference catheter. The catheter tracking system is arranged to sense the position of the reference catheter and thereafter to determine the position of the measurement catheter. To this end, the reference catheter must be fixed somewhere in or near the heart in such a way so as to maintain its position relative to the heart. For example, this might be inserted in the coronary sinus or the right ventricular apex. The coronary sinus is a small blood vessel that has its entrance in the auricle close to the inferior vena cava and the entrance to the right ventricle. The coronary sinus is of varying diameter but can be as much as 10 mm. The right ventricular apex is an area at the lower end of the right ventricle in the base of the heart. It is not a well-defined location and does not offer a very good fixing position for the reference catheter. As a result of a possible range of movement of the reference catheter, the known arrangement of reference and measurement catheters provides difficulties in positioning the measurement catheter accurately, in particular when in actual use in the heart.

Furthermore, the use of an additional catheter increases a risk of infections and renders the use of this known tracking system cumbersome.

SUMMARY OF THE INVENTION

In view of the drawbacks of the prior art, it is an object of the invention to provide a catheter tracking system and a method for tracking a catheter, which provides an improvement in accuracy and detection of a position of a catheter.

According to the present invention there is provided a catheter tracking system comprising a self referencing catheter, which self reference catheter comprises an inner core having at least one transducer on a head arranged at one end thereof, and an outer sheath adapted to movably receive the inner core, wherein the outer sheath comprises a plurality of sensors and a fixing means for fixing the outer sheath at a predetermined position, and wherein the sensors receive signals generated by the transducer, so as to produce measurement signals in accordance with a time of propagation of the signals for determining the position of the head relative to the outer sheath.

With an arrangement described above, a signal emitted from the transducer is received by at least two sensors provided at slightly different positions. From the time of propagation of the signals, the distances between the source of the signal and the respective sensors, at which the signal is received, can be calculated.

Since the positional relationship between the sensors is provided in accordance with a predetermined arrangement of sensors on the outer sheath, a position of the tip of the catheter from which signals were emitted may be determined in accordance with signals received by the sensors.

Advantageously, the sensors are arranged in the vicinity of the fixing means or even thereat, so that the determination of the relative position refers to a properly defined fixed point.

The fixing means may comprise an extendible cage which is advantageously arranged at a front end of the outer sheath. The cage may be mechanically extendible or may be of an inflatable type.

The sensors may be arranged in a form of an array extending along the outer sheath or may be arranged on protruding positions of the cage.

With the self referencing catheter, the catheter tracking system according to the invention only requires the introduction of a single catheter into the human or animal body. Thus, the risk of infection inherent with the introduction of a catheter can be reduced as compared to the prior art.

Additionally, the use of fluoroscopy (x-ray) can be substantially reduced so that the risks inherent to this technology can also be avoided.

Since the reference point, or in other words the fixing point of the outer sheath, is known, the relative position of the catheter head can be transferred into a three dimensional reference to positions on or in the heart, thereby providing a means whereby the catheter head may be returned to a desired point on or within the heart. This transfer can be supported by image processing means and methods which are well known in the art.

Furthermore, no modifications of the patient's support apparatus is required, which may be for example a theatre table, since the tracking system is substantially self-contained.

According to a second aspect of the present invention, the outer sheath can be provided with a plurality of transducers, and the head can be provided with a sensor.

In this case, signals can be used which are distinguishable by the sensor of the head. The signals can, for example, either have different frequencies or different timings, so that the respective source of the signal can be recognised.

It should be mentioned here that an increasing number of sensors provided at the head or at the outer sheath offers an increasing accuracy of the position since the number of defined points, to which reference can be made, increases.

For example, an improvement in the accuracy can be achieved, if the head and the outer sheath are each provided with a plurality of the respective devices. In this case, if an elongated head is used, a plurality of transducers or sensors thereon allows the determination of the angle of inclination of the head relative to the outer sheath.

The sensors may be acoustic sensors and the transducer an acoustic transducer and the propagation time may be the time of flight of acoustic signal.

The catheter tracking system may further be provided with a plurality of acoustic transducers acoustically coupled to and/or arranged on a human or animal torso for emitting acoustic signals into the torso. The system may further comprise a plurality of video cameras which operate to monitor a position of said transducers, and at least one acoustic sensor arranged on a tip of a catheter and adapted to receive the emitted acoustic signals. With such a system an absolute position of the tip of said catheter is determined on the basis of the monitored position of the transducers and a time of flight of the acoustic signals to said acoustic sensor.

In this case the time of flight of pulses, for example, ultrasonic vibrations are used to give the position of the catheter. Alternatively, ultrasonic pulses can be generated in the tip of the catheter and received by a number of transducers arranged in known positions. In the case of ultrasonics the propagation velocities in air and human tissue are very different. There is, it therefore, very strong reflection and refraction of the ultrasonic energy from the air-skin interface. For this reason and if required, the sensors can also be mounted on an operating table, provided the patient is made to lie in a pool of matching gel on the table. However, the presence of air in the lungs of the patient provides a preference for the ultrasonic signals to approach from the front of the chest. Therefore, advantageously the sensors or transducers may be mounted on the outside of the patient's chest. These would be secured using, say, a sticky index-matching material or straps. They could be positioned by the surgeon to give the best propagation to the heart (or part of the heart), for example avoiding the ribs.

In the case of externally mounted sensors their positions would need to be known. Hence it is proposed that the sensors be tracked using a known stereo video camera arrangement disclosed in our co-pending patent application Ser. No. 2287598A. With this arrangement the position of the sensors may be determined and tracked continuously. At least two cameras would be required, which would be mounted on a stand looking down on the patient's chest. In order to track the transducers the cameras must be able to see fiducial patterns of the sensors or transducers. If necessary the transducers may be placed under a surgical cover with the fiducial patterns visible above it, the fiducial patterns and the transducers being connected by, say, press fit studs.

The transducers emit ultrasound pulses in sequence and these are received by the sensor in the tip of the catheter. Comparison of the transmitted and received signals gives a time of flight of the signal. By applying alteration techniques in accordance with these measurements the position of the tip in three dimensions can be determined.

As hereinbefore mentioned, if the angle of the tip is to be measured, then the catheter may be provided with two receivers separated by a distance along the catheter. Alternatively, a number of receivers each with, say, a cardioid response could be used to enable the direction of propagation of the ultrasonic energy to be determined.

According to a third aspect of the present invention, there is provided a method for tracking a catheter, wherein the method comprises the steps of placing an outer sheath of a catheter at a predetermined position and fixing it by means of a fixing means, moving a head of a core movably received in said outer sheath into a position to be detected, emitting signals from a transducer arranged on the head, receiving the signals by means of a plurality of sensors arranged on the outer sheath, detecting the time of propagation of the signals between the transducer and each acoustic sensor, and calculating the position of the head relative to the outer sheath.

Alternatively, the signals can be emitted from a transducer arranged on the outer sheath, and can be received by a plurality of sensors arranged on the head.

Furthermore, the signals can be emitted by a plurality of transducers arranged on the outer sheath, and can be received by a simple sensor on the head. In this case however, the signals must be distinguishable by the sensor in order to correlate the received signal with the source from which it originates. This distinction of signals can either be achieved with signals having different frequencies or with signals having different timings.

Again, the sensors may be acoustic sensors and the transducers may be an acoustic transducer and the propagation time of the signals may be the time of flight of acoustic signals.

According to a further aspect of the present invention, there is provided a method for tracking a catheter comprising the steps of placing a plurality transducers on the human or animal torso, arranging a plurality of video cameras in a vicinity of the torso, so as to monitor a position of the transducers, introducing a catheter having a sensor on its tip into the torso, emitting signals from the transducers into the torso, receiving the emitted signals by means of the sensor, and correlating a position of the tip relative to said transducers, which is determined on a basis of a time of propagation of the signals, with the position of said transducers monitored by said video cameras, so as to obtain an absolute position of the tip of the catheter.

Again, the sensors may be acoustic sensors and the transducers may be acoustic transducers and the time of propagation of the signals may be the time of flight of acoustic signals.

For the evaluation of the obtained time of flight values, a correlation for different propagation velocities occurring in homogenous material can advantageously be used to improve the accuracy of the positional relationships obtained.

Corrections are applied to reduce the errors resulting from tissue inhomogeneity. This can be carried out by analysing the propagation times and in effect varying the assumed propagation velocity until the greatest degree of consistency is obtained for all the propagation times. Such analysis is useful when the velocity of propagation in the medium is unknown. They can be used to correct for the effects of small-scale inhomogeneity, due to blood vessels etc.

Alternatively, where a distance travelled by the acoustic signals is small, a variation in time of flight due to tissue inhomegenities may be ignored since an effect thereof introduces negligible errors.

Further advantageous modifications for carrying out the invention are depicted in the attached dependent claims.

The invention will hereinafter be described in detail by way of example only, with reference being made to the attached drawings in which;

DESCRIPTION OF THE PREFERRED EMBODIMENTS

Figure 1:
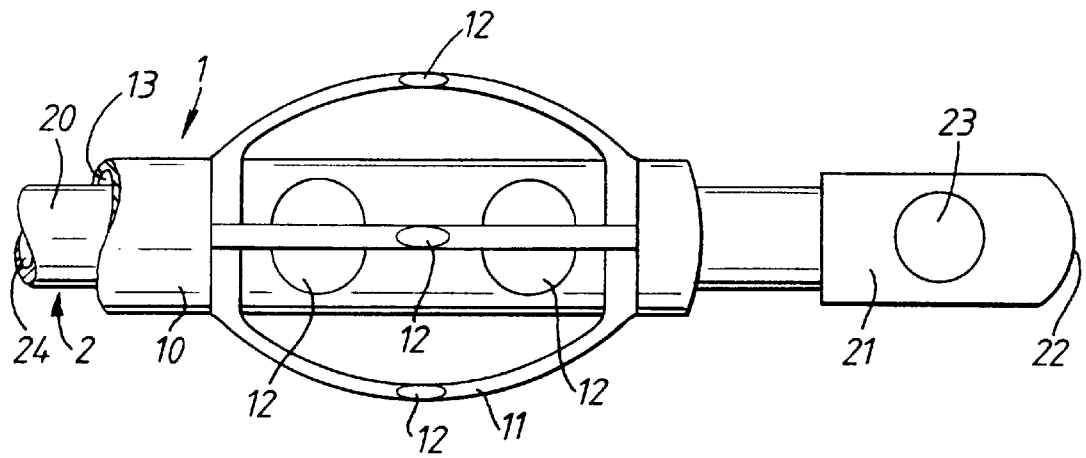
FIG. 1 shows a schematical diagram of an arrangement of a self referencing catheter.

FIG. 1 shows a front end of a self referencing catheter according to a first embodiment of the invention.

According to FIG. 1, there is provided an outer sheath generally referred to as 1, and a core or inner catheter, generally referred to as 2.

The outer sheath 1 has a pipe-shaped outer member or envelope 10, which has appropriate flexibility and stiffness to be inserted as a catheter into a blood vessel or the like. In the vicinity of the front end of the envelope 10, there is an extendible cage 11, which operates to increase the outer diameter of the outer sheath 1 at an end position thereof so as to be used as a fixing means for locking the end position of the outer sheath 1 at predetermined position. The cage 11, can be an inflatable cage or a mechanically operated cage. Such cages are well known in the art so that a detailed description of applicable working principles can be omitted here. It is to be noted that the cage 11, should be selected and arranged such that liquid can still pass the cage 11 in its extended state, in particular, when the outer sheath 1 is arranged and locked in a blood vessel. Further, the end portion of the outer sheath 1 is provided with acoustic sensors 12 which are arranged with a certain distance from each other. The sensors 12, are ultrasonic sensors adapted to receive an ultrasonic signal or pulse. The arrangement of the sensors 12, shown in FIG. 1, is merely an example; they can be arranged on the cage 11, or at different positions on the circumference of the envelope 10.

As seen in FIG. 1, the envelope 10, surrounds an inner catheter or a core 20, which is movably received in the envelope 10. The core 20, is rotatable within the envelope 10, as well as longitudinally movable therein. Advantageously, there is a certain play provided between the outer and the inner element, so as to form a free space 13, in which a wiring, piping or the like which extends along the outer sheath 1, can be received. The core 20, is advantageously a hollow body which provides an inner channel 24, for also receiving wiring or piping.

The core 20, has flexibility and stiffness properties which render it suitable to operate as a catheter. An end portion of the core 20, is provided with a head 21, with a measuring tip 22. The measuring tip 22, can be of any type for measuring electric currents, material properties or it can even operate as an optical device for visual inspection.

The measuring tip 22, can be replaced by, or combined with a means for providing a further functional tool such as a means for applying electrical current, laser light or the like. The tip can also be provided with a means for taking samples or for applying drugs, glue or the like.

According to FIG. 1, the head 21 is provided with an acoustic transducer 23. In this case, an ultrasonic transducer 23, is used for emitting ultrasonic signals or pulses to be received by the ultrasonic sensors 12, on the outer sheath 10.

The working principle of the device shown in FIG. 1 can be briefly described as follows:

The outer sheath 1, and the core 2, are introduced into a blood vessel or the like using well known techniques. When the portion of the outer sheath 1, provided with the cage 11, has reached a predetermined reference position, the cage 11 is extended so as to lock the outer sheath 1, at this position. The core 20, carrying the head 21, is then moved relative to the outer sheath 1 by moving within the envelope 10.

Acoustic signals are emitted by the acoustic transducer 23, arranged on the head 21. The acoustic signals are received by the acoustic sensors 12 on the outer sheath 1. Since the sensors 12 are arranged at different positions, a difference in the time of flight of a signal emitted by a single source 23, is obtained. From this difference, a position of the transducer 23, relative to the sensors 12, can be determined. Since the sensors 12, are locked to a known predetermined reference position by means of the cage 11, the actual position of the head 21, and, thus of the measuring tip 22, can be determined.

It should be noted here, that the number of sensors is not limited to two, with an increased number of sensors an even higher positional accuracy can be achieved.

Figure 2:
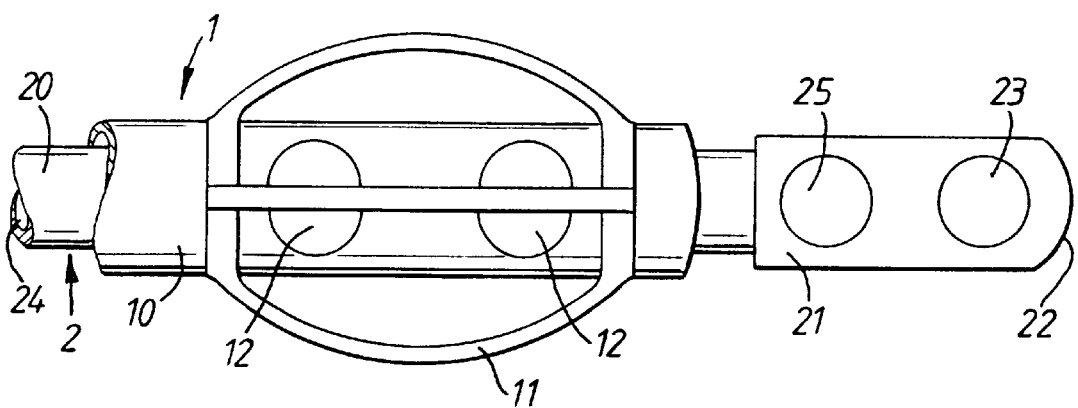
FIG. 2 shows a schematic diagram of a further arrangement of a self referencing catheter shown in FIG. 1.

FIG. 2 shows an advantageous modification of the embodiment described before in detail with reference to FIG. 1. The same reference signs denote the same parts as in FIG. 1, so that a repetition of this description can be omitted.

According to FIG. 2, the head 21, is provided with an additional transducer 25, for emitting acoustic signals. With this arrangement, the angle of inclination of the head 21, relative to the outer sheath 1, can be determined. For this purpose, the signals emitted by the transducers 23 and 25 must be distinguishable by the sensors 12. Distinction between the signals can either be achieved by different signal characteristics, for example, by frequency, or intensity, or by a simple offset in timing for emitting the signals.

Figure 3:
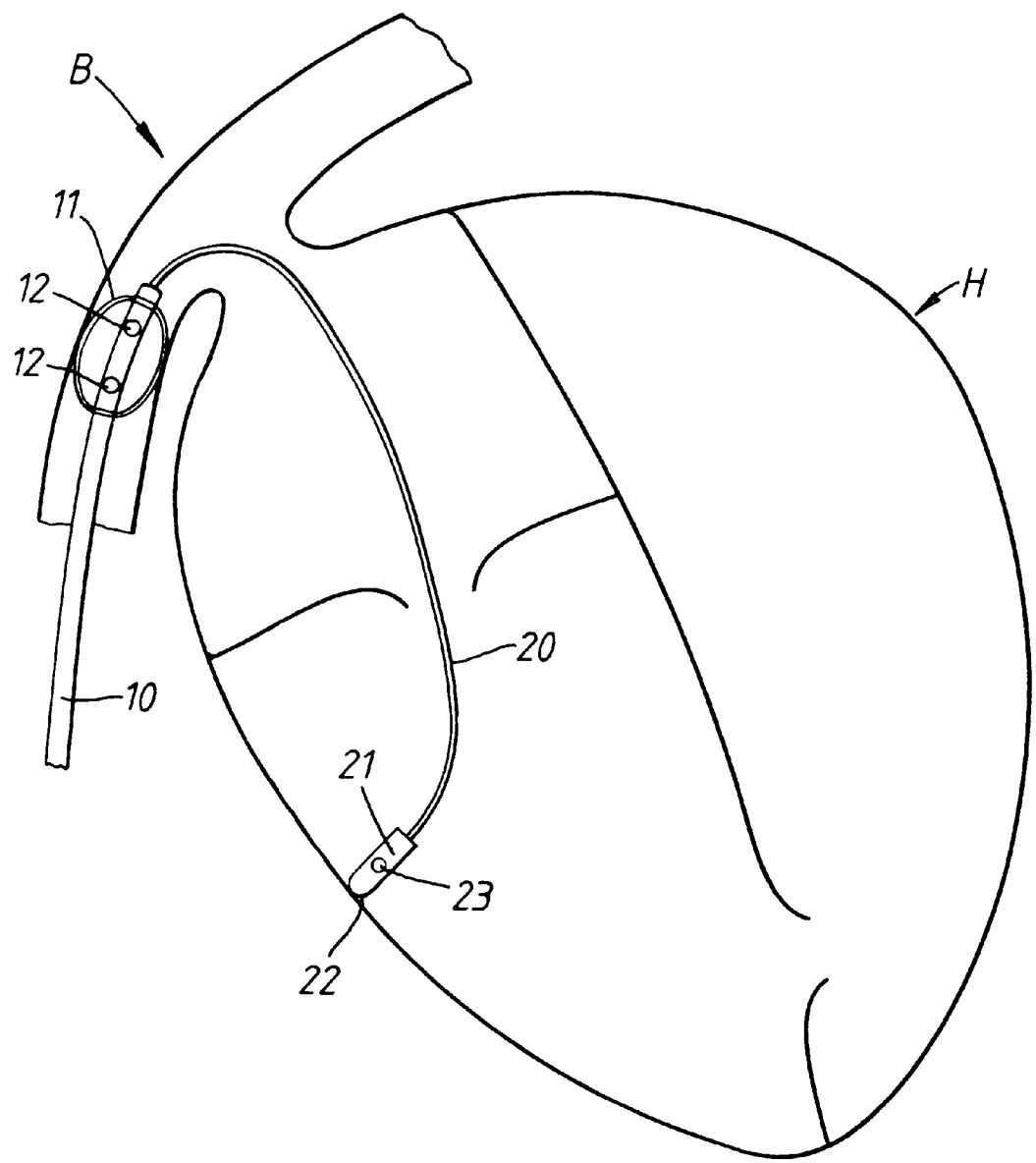
FIG. 3 is a schematic diagram of a self referencing catheter in use with a heart, and, FIG. 4 is a schematic conceptual diagram of a self referencing catheter in combination with a plurality of external sensors in use in a heart.

FIG. 3 shows an example for an application of the catheter shown in FIG. 1 in a heart. The heart H is connected to a variety of blood vessels B (e.g. vena cava or the auricle) into which the catheter is inserted in order to reach inner portions of the heart H. The reference signs used in FIG. 3 denote the same parts as in FIG. 1 so that a detailed description is omitted for the sake of brevity.

As can be clearly seen in FIG. 3, an envelope 10, of an outer sheath of a catheter is inserted into a blood vessel B. and is locked in a predetermined or suitable reference position by means of an extendible cage 11. The head 21 fixed to a core 20 is then moved into the heart H until the measuring tip 22 has reached the desired position(s). A transducer 23, and sensors 12, co-operate in the manner described with reference to FIG. 1 so as to monitor or track the actual position of the head 21 and the measuring tip 22, respectively. For this application, a synchronisation of the positional detection (i.e. emitting, receiving and evaluating signals) with the rhythm of the heartbeat is advantageous. However, this modification depends on the individual cases of application of the catheter.

It should be clear that the application to a heart is not limiting. Other organs or portions of a human or animal body can be the subject of application of the catheter tracking system. Also non-medical applications are possible, as long as a signal transfer between transducers and sensors is possible.

Figure 4:
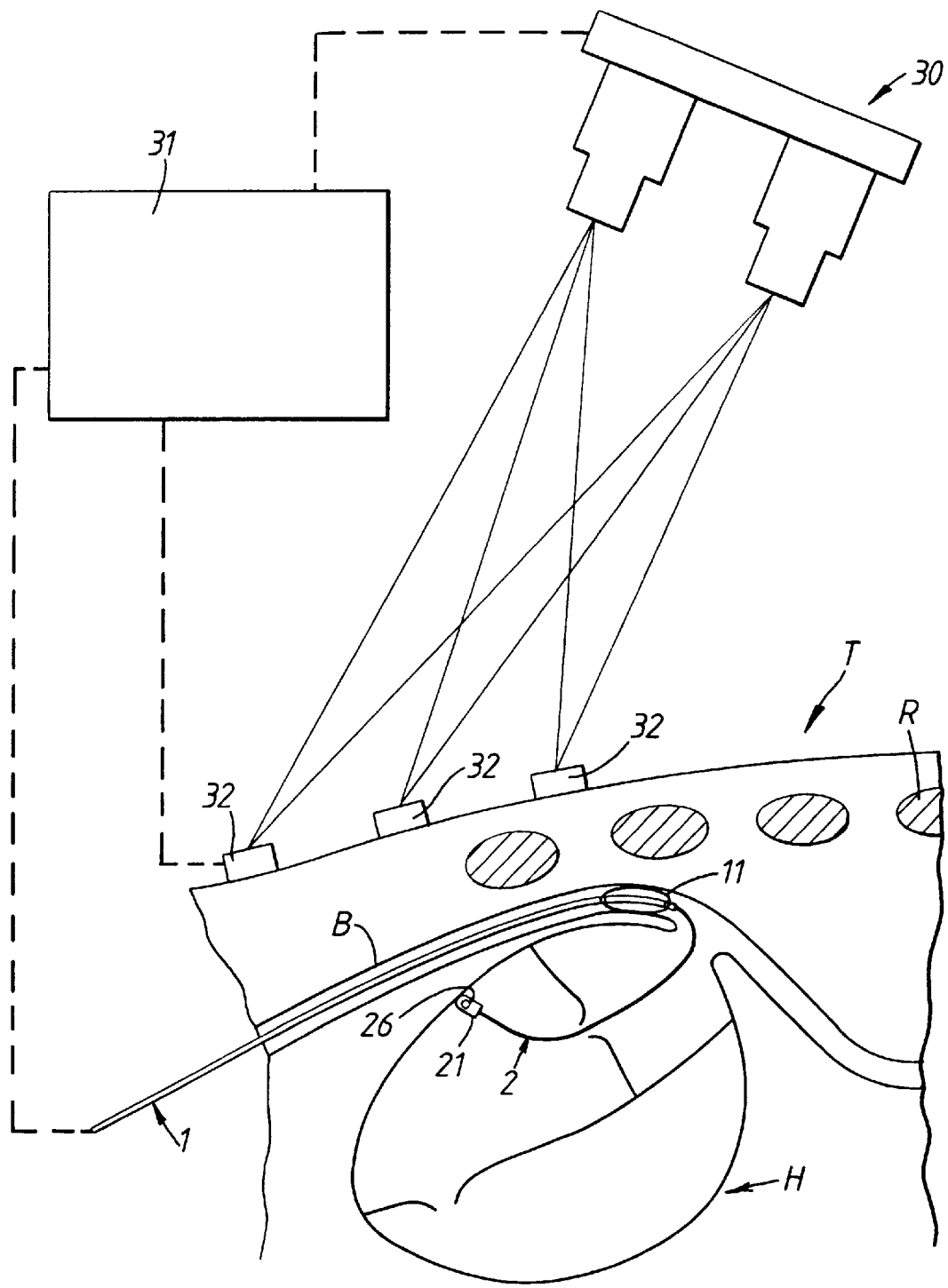

FIG. 4 depicts a further embodiment of the invention, applied to a human or animal heart in a torso by way of example. The same reference signs denote the same parts as in the foregoing figures, so that repetitions are omitted for the sake of brevity.

According to FIG. 4, there is partly shown a torso T with ribs R beneath which a heart H is accommodated. As seen from FIG. 4, a plurality of acoustic transducers 32, is arranged on the torso T. The transducers 32, are arranged such that the signals emitted therefrom pass between the ribs R. The ribs are considered opaque with respect to acoustic signals and can, additionally generate echo signals which may deteriorate the position sensing.

Above the torso T, there is arranged a stereo video-camera set 30, which is adapted to monitor the position of the transducers 32. The position of the transducers 32, is, thus, permanently known, even if the torso T is moved.

A catheter 1, 2, basically corresponding to the catheter described with reference to FIG. 1 is inserted via a blood vessel B into a heart H. In contrast to the embodiments described with reference to FIGS. 1 to 3, the outer sheath 1, of the catheter has no acoustic sensors arranged at an end position thereof. It is also possible to refrain from using an outer sheath, so that single catheter similar to the shown inner core 2, can be used. The head 21, of the core 2, is provided with a sensor 26, for receiving acoustic signals emitted by the transducers 32. From the detected differences in time of flight of the acoustic signals emitted from the transducers 32 and received by the sensor 26, a position of the head 21, relative to the transducers 32, is obtained, which in turn is correlated with the position of the transducers 32 monitored by the camera system 30, so as to finally obtain an absolute position of the head 21. The data is processed by a data processing means 31.

According to a modification, the end position of the outer sheath 1, which is locked by means of a cage 11, as described in the foregoing embodiments, can also be provided with sensors so that a position of a reference point for the heart which moves in the torso, at least due to its heart beat, can also be monitored by means of the transducers 32, and the camera system 30.

It should be mentioned here that for simplification purposes, the transducers 32, can be replaced by sensors, whereas the sensor 26 can be replaced by a transducer forming the single source for an acoustic signal. Furthermore, the cage 11, may also be provided with sensors or transducers and arrangement of signals generated from the catheter head, the cage or externally positioned transducers may serve to provide the position of the catheter head 22, with reference to the cage and/or externally positioned transducers.

I claim:

1. A self-referencing catheter for a catheter tracking system, the catheter comprising:
   an outer sheath member;
   deployable fixing means mounted on the outer sheath member for fixing the outer sheath member at a predetermined position within a body into which the catheter is inserted;
   an inner core member slidably mounted within the outer sheath member, the inner core member having a head portion formed thereon which carries transducer means for generating signals; and
   sensing means located on the deployable fixing means for receiving signals from the transducer means and for producing measurement signals indicative of the location of the head portion with respect to the deployable fixing means in accordance with time propagation of signals generated by the transducer means and received by the sensing means.

2. A catheter as claimed in claim 1, wherein the head portion further comprises a measurement sensor for sensing electrical signals in a heart.

3. A catheter as claimed in claim 2, wherein the head portion further comprises means for treating adjacent tissue in-situ.

4. A catheter as claimed in claim 1, wherein the deployable fixing means comprises an extendible cage.

5. A catheter as claimed in claim 1, wherein the sensing means comprises a plurality of sensors arranged in an array.

6. A catheter as claimed in claim 1, wherein the transducer means comprises a plurality of transducers arranged in an array.

7. A catheter as claimed in claim 1, wherein the head portion of the catheter is provided with inner core member comprises an array of transducers for determining an inclination angle of the said head portion with respect to the deployable fixing means.

8. A catheter as claimed in claim 1, further comprising signal processing means for processing the signals received.

9. A catheter as claimed in claim 1, wherein the transducer means comprises at least one acoustic transducer which generates acoustic signals, and wherein the sensing means comprises at least one acoustic sensor for receiving the acoustic signals generated.

10. A catheter as claimed in claim 9, wherein the acoustic signals are ultrasonic signals.

11. A self-referencing catheter comprising:
    an outer sheath member;
    deployable fixing means mounted on the outer sheath member for fixing the outer sheath member at a predetermined position within a body into which the catheter is inserted;
    transducer means located on the outer sheath for generating signals; and
    an inner core member slidably mounted within the outer sheath member, the inner core member having a head portion formed thereon which carries sensing means for receiving signals from the transducer means and for producing measurement signals indicative of the location of the head portion with respect to the deployable fixing means in accordance with time propagation of signals generated by the transducer means and received by the sensing means.

12. A catheter as claimed in claim 11, wherein the head portion of the inner core member comprises an array of sensors for determining an inclination angle of the head portion with respect to the deployable fixing means.

13. A catheter as claimed in claim 11, wherein the head portion further comprises a measurement sensor for sensing electrical signals in a heart.

14. A catheter as claimed in claim 11, wherein the head portion further comprises means for treating adjacent tissue in-situ.

15. A catheter as claimed in claim 11, wherein the deployable fixing means comprises an extendible cage.

16. A catheter as claimed in claim 11, wherein the sensing means comprises a plurality of sensors arranged in an array.

17. A catheter as claimed in claim 11, wherein the transducer means comprises a plurality of transducers arranged in an array.

18. A catheter as claimed in claim 11, further comprising signal processing means for processing the received signals.

19. A catheter as claimed in claim 11, wherein the transducer means comprises at least one acoustic transducer which generates acoustic signals and wherein the sensing means comprises at least one acoustic sensor for receiving the acoustic signals generated.

20. A catheter as claimed in claim 19, wherein the acoustic signals are ultrasonic signals.

21. A method for tracking a catheter comprising an outer sheath member, deployable fixing means mounted on the outer sheath member for fixing the outer sheath member at a predetermined position within a body into which the catheter is inserted, an inner core member slidably mounted within the outer sheath member, the inner core member having a head portion formed thereon which carries transducer means for generating signals, and sensing means located on the deployable fixing means for receiving signals from the transducer means and for producing measurement signals indicative of the location of the head portion with respect to the deployable fixing means in accordance with time propagation of signals generated by the transducer means and received by the sensing means, the method comprising the steps of:

placing the outer sheath member at a predetermined position within the body;

deploying the deployable fixing means to fix the catheter in the predetermined position;

moving the head portion of the inner core member into a position within the body to be detected;

generating signals from the transducer means carried by the head portion of the inner core member;

transmitting the generated signals;

receiving the generated signals at the sensing means on the deployable fixing means;

determining a propagation time for the signals between the transducer means and the sensing means; and calculating the position of the head portion relative to the deployable fixing means using the propagation time determined.

22. A method as claimed in claim 21, wherein the transducer means comprises at least one acoustic transducer which generates acoustic signals and the sensing means comprises at least one acoustic sensor for receiving the acoustic signals generated.

23. A method as claimed in claim 21, wherein said outer sheath member is positioned and fixed in a blood vessel.

24. A method for tracking a catheter comprising an outer sheath member, deployable fixing means mounted on the outer sheath member for fixing the outer sheath member at a predetermined position within a body into which the catheter is inserted, transducer means located on the outer sheath for generating signals, and an inner core member slidably mounted within the outer sheath member, the inner core member having a head portion formed thereon which carries sensing means for receiving signals from the transducer means and for producing measurement signals indicative of the location of the head portion with respect to the deployable fixing means in accordance with time propagation of signals generated by the transducer means and received by the sensing means, the method comprising the steps of:

placing the outer sheath member at a predetermined position within the body;

deploying the deployable fixing means to fix the catheter in the predetermined position;

moving the head portion of the inner core member into a position within the body to be detected;

generating signals from the transducer means located on the outer sheath;

transmitting the generated signals;

receiving the generated signals at the sensing means on the head portion of the inner core member;

determining a propagation time for the signals between the transducer means and the sensing means; and calculating the position of the head portion relative to the deployable fixing means using the propagation time determined.

25. A method as claimed in claim 24, wherein the transducer means comprises at least one acoustic transducer which generates acoustic signals and wherein the sensing means comprises at least one acoustic sensor for receiving the acoustic signals generated.

26. A method as claimed in claim 24, wherein the outer sheath member is positioned and fixed in a blood vessel.

* * * * *